United States Patent [19]
Druais

[11] Patent Number: 5,807,387
[45] Date of Patent: Sep. 15, 1998

[54] OPTICAL DESIGNATION DEVICE ESPECIALLY FOR MICROSURGICAL OPERATIONS

[75] Inventor: Herve Druais, Seyssinet, France

[73] Assignee: Deemed International, S.A., Gieres, France

[21] Appl. No.: 612,933

[22] PCT Filed: Sep. 6, 1994

[86] PCT No.: PCT/FR94/01049

§ 371 Date: May 20, 1996

§ 102(e) Date: May 20, 1996

[87] PCT Pub. No.: WO95/07054

PCT Pub. Date: Mar. 16, 1995

[30] Foreign Application Priority Data

Sep. 7, 1993 [FR] France ................................. 93 10625

[51] Int. Cl.⁶ ...................................................... A61N 5/06
[52] U.S. Cl. ................................ 606/10; 606/13; 606/14; 606/130; 219/121.78; 600/476

[58] Field of Search .................................. 606/2–19, 130; 356/1, 12, 18, 149, 375; 219/121, 78, 121.82; 607/88–92; 128/664; 600/476

[56] References Cited

U.S. PATENT DOCUMENTS

| 5,143,076 | 9/1992 | Hardy et al. | 128/664 |
| 5,545,160 | 8/1996 | O'Rourke | 606/10 |
| 5,562,656 | 10/1996 | Sumiya | 606/4 |

*Primary Examiner*—David M. Shay
*Attorney, Agent, or Firm*—Weiser and Associates, P.C.

[57] ABSTRACT

Optical designating device, especially for use in microsurgery, comprising a tool-carrier stage (2) integral with the optical instrument (1), supporting at least one light source (4, 5) for emitting a light beam (6, 7), said light source (4, 5) being offset in relation to the optical axis (10) of the optical instrument (1). The orientation of the light source (4, 5) in relation to the optical axis (10) of the microscope is determined in order to aim the light beam (6, 7) at a target point (15).

10 Claims, 1 Drawing Sheet

OPTICAL DESIGNATION DEVICE ESPECIALLY FOR MICROSURGICAL OPERATIONS

BACKGROUND OF THE INVENTION

1. Field of the Invention

The present invention concerns a device of optical designation, especially for the realization of operation of microsurgery. A such device is destined to be associated to an optical instrument such as a microscope or a binocular. In the following, we will designate by "microscope" all optical instruments employed for the observation of the zone of intervention in surgery and microsurgery.

2. Description of the Related Art

Such microscopes are employed to permit the surgeon to effect manipulations of precision. One of the problems is to manoeuver around a target within the field of vision of the microscope. Another problem is to exploit the information obtained by techniques of imagery, for example tomodensitometry and nuclear magnetic resonance, to guide the gestures of the surgeon.

It is known for example in the state of the technique the French patent FR2682778, concerning a microscope for operation of stereotaxic microsurgery assisted by computer. This document describes a microscope for stereotaxic microsurgery assisted by computer and a process for its functioning. This microscope consists of detectors detecting optical givens, a system of identification of position and a device of control of the process evaluating the signals of the aforementioned system, this system is a system at base optical integrated into the optical system of the microscope. It is foreseen a device which converts the signals delivered by the device into a two-dimensional graphic representation. Such a microscope presents a great complexity to put into work and is not adapted to the daily work of a surgeon.

We know equally in the earlier art a system of localization described in the U.S. Pat. No. 5,143,076. This system consists of a framework integrated with the head of the patient. The framework supports light sources whose intersection designates a particular zone of the head of the patient, for example, the target. This system is not totally satisfactory for it does not permit to take count of the simple manner of the displacement of the microscope, and limits the ways of access by the fact of the presence of the framework supporting the light sources.

SUMMARY OF THE INVENTION

A primary goal of the present invention is to propose a simple way permitting the surgeon to supervise the approach to the critical zone, or target, without quitting the eyepiece of the microscope.

A secondary goal of the invention is to permit a calculation of the distance between the observed surface and the target in such a way as to determine the depth between the target in relation to the surface of the operating field.

A third goal of the invention is to permit control of the ways of manoeuvering to permit a following of the target notwithstanding the relative movements of the microscope in relation to the observed field, and eventually a subjection of the methods of designation in relation to a base of pre-recorded images.

The invention concerns most particularly a device of optical designation consisting of a plate integrated with the optical instrument, supporting at least one light source for the emission of a light beam, said light source orientable angularly, said light source being shifted in relation to the optical axis of the optical instrument.

The surgeon can thus evaluate visually the progression of his work.

According to a first variant, the orientation of the light source in relation to the optical axis of the microscope is determined by a computer assuring the orientation of the light beam in the direction of a target-point whose coordinates are known.

According to a second variant, the orientation of the light source is subject to the displacement of the microscope. This method of realization permits to realize a following of the target notwithstanding the relative displacements of the microscope in relation to the operating field.

According to a third variant, the device consists of a sensor of angular position delivering an electric signal permitting a computer to determine the depth of the target in function of the angular position of the light source in relation to the optical axis of the microscope on the one hand, and of the focal distance of the microscope on the other.

According to a preferred mode of realization, the device of optical designation according to the invention consists of a plurality of light sources shifted in relation to the optical axis of the microscope, distributed symmetrically in relation to the optical axis of the microscope. Advantageously, the angular position in relation to the optical axis of each of the light sources is controlled by a motorized means controlled by a computer in such a way as to assure the convergence of the light beams generated by the light sources at a target point whose coordinates are known.

Advantageously, the computer controls the motorized methods of orientation of each of the light sources in a way that assures the convergence of each of the beams, on the one hand, and of the optical axis, on the other, at a target point whose coordinates are known.

Preferably, the device of optical designation according to the invention incorporates, in addition, an electronic memory containing a bank of Image givens, the computer determining the coordinates of the target in accordance with the information coming from the sensors of position delivering a signal function of the relative position of the microscope in the referential object.

BRIEF DESCRIPTION OF THE DRAWINGS

The invention will be better understood by a reading of the description that follows, making reference to the annexed diagrams in which the unique FIGURE represents a schematic view of the device of optical designation.

DETAILED DESCRIPTION

Figure 1:
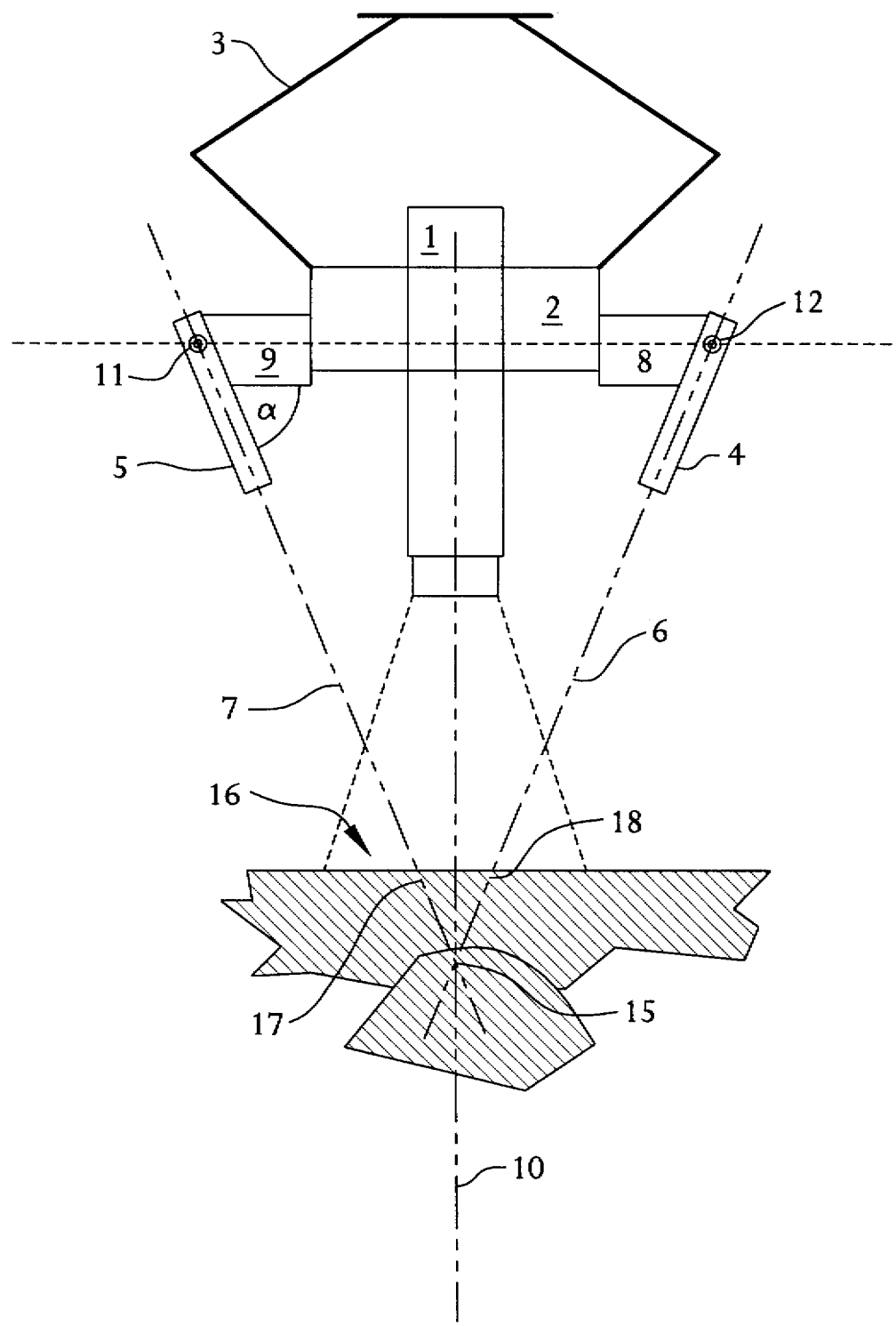

The unique FIGURE represents a schematic view of the device of optical designation according to the invention. It consists of an optical instrument (1) of a known type, mounted on a tool-holding plate (2) integrated with an articulated support (3).

The device includes in the described example two sources of light (4, 5), for example of LASER type, integrated with the tool-holding plate (2). The two light sources (4,5) emit beams weakly diverging whose optical axes are referenced (6, 7).

The optical sources are disposed on the extensions (8, 9) of the tool-holding plate (2) supporting the optical instrument (1) in such a way as to shift the two light sources symmetrically in relation to the principal optical axis (10).

The light sources (4, 5) are angularly mobile in relation to pivots (11, 12) tangential in relation to an imaginary disk having for its axis of symmetry the principal optical axis (10). The positioning of the light sources can be assured manually, but by preference it is motorized. To this effect, the device includes, for each of the light sources (4, 5), an electric motor and the case demanding a reduction gear assembly assuring the angular displacement of the light sources (4, 5) in accordance with the signals of control coming from a computer receiving information coming from a base of Image givens in which are recorded the images coming from a system of imagery, and permitting to calculate the position of a target in the referential of the patient and/or receiving information coming from the sensors that recopy the position of the articulated support (2), and permitting to calculate the position of the microscope within a fixed referential.

If not, the angular orientation of the light sources (4, 5) is determined in such a way as to converge at a target-point (15).

The target point can for example be constituted by the surface of a blood vessel, a nerve or an organ that it is advisable to not attain during the surgical intervention.

The shift between the surface observed by the operator, and the target point translates to a staggering of the two visible spots at the intersection between the observed surface (16) and the light beams (6,7). This displacement is reduced proportionately as the target-point (15) is approached.

In another way, the distance between the two spots (17, 18) permits to deduce the depth of the target-point (15) in relation to the observed surface (16) by a calculation of triangulation:

$$P = (E/2 * tg\ a) - L$$

Where

P designates the depth of the target in relation to the observed surface

E designates the displacement of the two light sources a designates the angle formed by the light beams (6, 7) in relation to a plane perpendicular to the principal optical axis (10)

L designates the distance between the plane of the two light sources (4, 5) and the observed surface.

This distance L is determined by the characteristics and the adjustments of the microscope because it is a function of the distance between the objective and the observed surface and therefore of the adjustment of the optical system permitting to obtain a sharp image.

The result of this calculation can be viewed in the eyepiece of the optical system or on any display system of a known type. According to a third mode of utilization, one realizes a measure of the depth of the target (15) without prior knowledge of the distance between the observed surface and the optical instrument.

To this effect, the distance between the observed surface and the plane passing through the two light sources (4, 5) is determined by making the beams (6, 7) converge at a single point of the observed surface (18) in such a way as to superimpose the two spots (17, 18).

One registers thus the angular orientation a1 of the optical beams. The step following consists in controlling the orientation of the beams (6, 7) in such a ways as to make them into a single point (15) of the target. The beams present thus a new orientation "a" which permits to determine the depth of the target in relation to the observed surface in application of the following equation:

$$p = \frac{E(tg\ a - tg\ a1)}{2}$$

Where:

p designates the depth of the target in relation to the observed surface

E designates the distance between the two light sources a designates the angle formed by the light beams (6, 7) in relation to a plane perpendicular to the principal optical axis (10).

a1 designates the angle initially formed by the light beams (6, 7) in relation to a plane perpendicular to the principal optical axis (10), and assuring the convergence of the two spots (17, 18) on the observed surface.

It is equally possible to proceed to an evaluation of the depth of the target from the displacement e of the two light spots (17, 18). The depth of the target is in this case determined as follows:

$$p = e\frac{tg\ a}{2}$$

Where:

p designates the depth of the target in relation to the observed surface e designates the distance between (displacement of) the two light spots a designates the angle formed by the light beams (6, 7) in relation to a plane perpendicular to the principal optical axis (10).

The displacement e of the light spots can be measured or evaluated in a known fashion by a calibrated grid visible through the optical instrument or by another equivalent method.

The device according to the invention permits of visual surveillance of the approach of the target-point and moreover to display the calculated distance. The surgeon can thus adapt in an optimal fashion his operational gestures.

According to another mode of utilization, one realizes a following of the target. While the depth of the target is known by one of the preceding methods, it is possible to control the angular orientation of the light sources (4, 5) by applying the following trigonometric formula:

$$a = \mathrm{arc}tg\left(\frac{2L + 2P}{E}\right)$$

After the determination of the initial angular orientation, it is possible to subject the angular variation to the displacements of the optical system whose utilization tries to conserve the focalization on the observed surface, which permits to deduce the evolution of the depth of the target in proportion (in accordance) with the progression of the surgical intervention.

The determination of the angular position of the light sources (4, 5) is assured by the angular electric sensors, electro-mechanical or optronical of a known type. They deliver the electrical signals put out by a computer for the recalculation of the orientation of each of the light beams in accordance with the displacements of the support (2) within the fixed referential.

By way of example, the device is used according to successive modes:

acquisition of the initial orientation of the light sources directed so as to assure the convergences of the spots on the observed surface;

initial displacement of the light sources in order to designate the target (15);

displacements of the light sources subjected to the movements of the optical instrument.

The invention is described in this which precedes by way of non-limited example. It is understood that the Man of the Work (the expert) will be able to propose numerous variations and adaptations without leaving the framework of the invention. In particular, the example of the realization described consists of two spots placed symmetrically within the plane perpendicular to the axis of observation of the microscope. It is, of course, possible to foresee a different number of spots and to place these spots in an asymmetrical fashion.

I claim:

1. A device of optical designation, comprising:

(a) an optical instrument having a principle optical axis and permitting a user to observe a surface corresponding to a patient;

(b) at least two light sources, each adapted to generate a light beam and each pivotally mounted in relation to the optical instrument such that the light beam and the principle optical axis intersect approximately at a target point corresponding to a target;

(c) means for controlling orientation of the light sources; and (d) means for determining a depth between the observed surface and the target point, wherein the device operates in:

(A) an initial acquisition mode in which the light sources are converged on the observed surface to determine the normal distance L between the observed surface and a plane passing through the light sources and perpendicular to the principle optical axis, based on the following equation:

$P = E/2 * tg\ a$ wherein E is the distance between the light sources and a is the angle between the light beams and the plane;

(B) an initial target displacement mode in which the light sources are converged on the target to determine the depth P of the target below the observed surface, based on the following equation:

$P = (E/2 * tg\ a) - L$ and (C) an normal operating mode;

in which the depth P of the target below the observed surface is updated when L and a are constant, based on the following equation $P = e/2tg\ a$ wherein e is the distance between two light spots on the observed surface formed by the two light sources;

in which the angle a is automatically updated to control the light sources to follow the target when L changes as the optical instrument translates along the principle optical axis, based on the following equation:

$$a = \text{arc}tg\left(\frac{2L + 2P}{E}\right)$$

and in which the angle a is automatically updated to control the light sources to follow the target when L changes as a result of the observed surface moving with respect to the optical instrument.

2. The invention of claim 1, wherein the light beams are weakly diverging.

3. The invention of claim 1, further comprising means for displaying the depth within an eyepiece of the optical instrument to enable the user to supervise approach to the target without quitting the eyepiece.

4. The invention of claim 1, wherein said means for controlling controls the orientation of the light sources to follow the target notwithstanding relative movements between the optical instrument and the target.

5. The invention of claim 1, wherein:

the device comprises two light sources generating weakly diverging light beams; and said means for controlling comprises:

(1) a tool-holding plate integrated with an articulated support controlling the position of the optical instrument and two extensions, each pivotally mounting one of the light sources;

(2) one or more motors controlling the orientation of the light sources relative to the tool-holding plate; and (3) a computer:

(i) determining and controlling the orientation of the light sources relative to movements between the optical instrument and the target; and (ii) determining and displaying the depth in an eyepiece of the optical instrument to enable the user to supervise approach to the target without quitting the eyepiece, wherein the computer uses a base of image givens to calculate position of the target in a referential of the patient and to control the orientation of the light sources.

6. The invention of claim 1, wherein the means for controlling comprises a tool-holding plate integrated with (i) an articulated support controlling the position of the optical instrument and (ii) one or more extensions, each pivotally mounting one of the light sources.

7. The invention of claim 6, wherein said means for controlling further comprises one or more motors controlling the orientation of the light sources relative to the tool-holding plate.

8. The invention of claim 1, wherein said means for determining comprises a computer.

9. The invention of claim 8, wherein the computer:

(1) determines and controls the orientation of the light sources relative to movements between the optical instrument and the target; and (2) determines and displays the depth in an eyepiece of the optical instrument.

10. The invention of claim 8, wherein the computer uses a data base of images to calculate position of the target in a referential of the patient and to control the orientation of the light sources.

* * * * *

UNITED STATES PATENT AND TRADEMARK OFFICE
CERTIFICATE OF CORRECTION

PATENT NO. : 5,807,387
DATED : September 15, 1998
INVENTOR(S) : Herve Druais

It is certified that error appears in the above-identified patent and that said Letters Patent is hereby corrected as shown below:

```
On the title page: Item [73] Assignee: ELEKTRA IGS, S.A., Gieres,
France".
```

Signed and Sealed this

Seventeenth Day of August, 1999

Attest:

Q. TODD DICKINSON

Attesting Officer

Acting Commissioner of Patents and Trademarks